(12) United States Patent
Urey et al.

(10) Patent No.: US 9,846,115 B2
(45) Date of Patent: Dec. 19, 2017

(54) MINIATURIZED INTEGRATED MICRO ELECTO-MECHANICAL SYSTEMS (MEMS) OPTICAL SENSOR ARRAY FOR VISCOSITY AND MASS DETECTION

(71) Applicant: KOC UNIVERSITESI, Istanbul (TR)

(72) Inventors: Hakan Urey, Istanbul (TR); Goksenin Yaralioglu, Istanbul (TR)

(73) Assignee: KOC UNIVERSITESI, Istanbul (TR)

( * ) Notice: Subject to any disclaimer, the term of this patent is extended or adjusted under 35 U.S.C. 154(b) by 0 days.

(21) Appl. No.: 14/917,574

(22) PCT Filed: Sep. 9, 2013

(86) PCT No.: PCT/IB2013/058407
§ 371 (c)(1),
(2) Date: Mar. 8, 2016

(87) PCT Pub. No.: WO2015/033190
PCT Pub. Date: Mar. 12, 2015

(65) Prior Publication Data
US 2016/0223456 A1    Aug. 4, 2016

(51) Int. Cl.
*B01L 3/00* (2006.01)
*G01N 21/17* (2006.01)
(Continued)

(52) U.S. Cl.
CPC ...... *G01N 21/1702* (2013.01); *B01L 3/50273* (2013.01); *B01L 3/502715* (2013.01);
(Continued)

(58) Field of Classification Search
CPC .... G01N 21/1702; G01N 21/17; G01N 21/00; G01N 11/16; G01N 11/10; G01N 11/00;
(Continued)

(56) References Cited

U.S. PATENT DOCUMENTS

2005/0009197 A1* 1/2005 Adams .................. G01Q 70/08
436/164
2008/0245135 A1* 10/2008 Aubin ...................... G01N 5/02
73/61.49

FOREIGN PATENT DOCUMENTS

WO    WO2008018834 A1    2/2008
WO    WO2012059828 A2    5/2012

OTHER PUBLICATIONS

Nistor, Corneliu, Magneto-optical studies of field-driven propagation dynamic of domain walls in Permalloy nanowires and scaling of magnetic energy losses in Permalloy films and microstructures, Dissertation, The University of Texas at Austin, Aug. 2006, pp. 1-108.*

(Continued)

*Primary Examiner* — Christine T Mui
(74) *Attorney, Agent, or Firm* — Gokalp Bayramoglu (57) ABSTRACT

The present invention relates generally to the field of chemical and biological sensors and in particular to micro electromechanical systems (MEMS) sensors for measuring fluid viscosity and detection of minute amounts of chemicals and biological agents in fluids. It is an object of the present invention to provide a sensor that will work in disposable cartridges with remote sensing that can measure dynamic changes of the functionalized cantilevers in liquid and gas environment.

17 Claims, 9 Drawing Sheets

(51) Int. Cl.
*G01N 11/16* (2006.01)
*G01N 29/02* (2006.01)
*G01N 5/00* (2006.01)
*G01N 29/24* (2006.01)

(52) U.S. Cl.
CPC .......... B01L 3/502761 (2013.01); G01N 5/00 (2013.01); G01N 11/16 (2013.01); G01N 29/022 (2013.01); G01N 29/2418 (2013.01); B01L 2300/06 (2013.01); B01L 2300/0654 (2013.01); B01L 2300/16 (2013.01); B01L 2300/18 (2013.01); G01N 2201/062 (2013.01); G01N 2201/068 (2013.01); G01N 2201/06113 (2013.01); G01N 2201/08 (2013.01); G01N 2291/012 (2013.01); G01N 2291/0256 (2013.01); G01N 2291/02818 (2013.01); G01N 2291/0427 (2013.01)

(58) Field of Classification Search
CPC .......... B01L 3/502715; B01L 3/50273; B01L 3/5027; B01L 3/502; B01L 3/50
USPC .... 422/69, 68.1, 50, 82.05, 82.09, 502, 501, 422/500
See application file for complete search history.

(56) References Cited

OTHER PUBLICATIONS

Onur Cakmak et al "Microcantilever Base Disposable Viscosity Sensor for Serum and Blood Plasma Measurements" Methods, vol. 63, No. 3, Jul. 20, 2013, pp. 225-232.

\* cited by examiner

MINIATURIZED INTEGRATED MICRO ELECTO-MECHANICAL SYSTEMS (MEMS) OPTICAL SENSOR ARRAY FOR VISCOSITY AND MASS DETECTION

FIELD OF THE INVENTION

The present invention relates generally to the field of chemical and biological sensors and in particular to a micro electro-mechanical systems (MEMS) sensors for measuring fluid viscosity and detection of minute amounts of chemicals and biological agents in fluids.

BACKGROUND

Detecting small amounts of chemicals and substances in liquids have many applications in chemistry and biology. In medicine, for example, one can diagnose many diseases by detecting chemicals (sodium, nitrides, calcium, potassium, cardiac markers, etc.) and their concentrations in bodily fluids such as blood, urine, saliva etc. Detecting pathogens (Tuberculosis, Hepatitis, HIV viruses, etc.) in bodily fluids as well as in the environment is also area of active research and development.

Similarly measuring fluid viscosity has also great interest in industrial applications and medicine. The ability to gather data on viscosity gives manufacturer important information on how to design fluidic systems. Especially in microfluidic systems viscosity determines the pumpability of the fluids and pressure drops across the channels. For example, viscosity of inks is very crucial for inkjet printing systems. In automotive industry, it is necessary for lubricant manufacturers to know the viscosity of their lubricants developed for different parts of the car engine and hydraulic systems.

In medicine, blood viscosity and coagulation time measurements are used for the diagnosis of several diseases such as cardiovascular disorders, rheumatoid arthritis, and certain autoimmune diseases. Patients who use blood thinners need to monitor their blood viscosity and coagulation time continuously.

The sensor requirement for the above sensing areas can be addressed by vibrating mechanical structures. Especially microcantilevers find various applications based on advantages such as lower detection limits due to miniaturization, the ability of shape optimization of cantilevers, the ability to selectively place functionlized regions on the these cantilevers (also interchangeably called "microcantilevers"), and the possibility of working on large arrays which can be integrated with optics and electronics.

When these cantilevers are placed in liquid, the dynamics of the vibration (phase and amplitude) are influenced by the viscosity of the liquid and the mass accumulation on the cantilevers. By measuring the vibration phase and/or amplitude one can detect liquid viscosity and minute amounts of chemicals and substances that may exist in the liquid. Furthermore, the cantilevers can be set into oscillation using a feedback circuitry. In this case, frequency measurement can be used to monitor dynamic changes of the cantilever vibration.

To address the measurement needs for viscosity and mass, various methods have been proposed. Some of the disadvantages of these currently known types of sensors are; that they require electrical connections (also called electrical conductors) to couple the sensor to a detector, limited optical detection options, limitations to gas phase detection, sensors that use frail readout components (for example, Doppler vibrometry), readouts that can be affected by refractive index variations due to monitoring of the deflection, sensors with no immunity against environmental noise, and the inability to heat the cantilever/samples during sensing. Further, it is believed that current alternatives to parallel sensing are limited to laboratory use only. It is therefore desirable to have a fieldable, label-free demonstrator, which is missing due to the lack of various components including a suitable readout mechanism that can be utilized in an array setting, a package that would protect functionalized surfaces during shelf life, which usually requires handling of liquids, and an integrated approach that would allow disposal of certain components, whereas others remain for the next use (for example, disposable cartridges containing the MEMS sensor array).

One objective of this invention is to enable a MEMS sensor array having a sensor array that is miniaturized, highly selective, highly sensitive, parallel, label-free and/or portable. Such a sensor array will provide a valuable tool for point-of-care diagnostics, and chemical sensing with its capabilities of a single analyte or a multianalyte screening and data processing. In addition such a sensor can measure dynamic properties of bodily fluids such as viscosity, fluid damping and chemical changes of the liquid. It is a further objective of these sensor arrays to increase sensitivity and specificity to possibly increase the likelihood of early diagnosis as well as the suitability of treatment assistance, such as dosage advice. It is envisioned that this may lead to increased effectiveness of doctor-patient interaction and personalized guidance. It is believed that such systems that meet the demands of parallel, label-free, and highly selective sensing do not exist today as microsystem technologies and readout methods cannot meet expectations for various reasons including: robustness issues associated with functional surfaces and the lack of a truly integrated, array-compatible readout techniques. Alternatively, it is believed that microarray technologies can offer parallel and selective detection, but are not fieldable as they require expertise to run and maintain and require expensive infrastructure due to complex labeling and sensing methods. While many fieldable applications, such as pregnancy test kits or the glucose sensor exist, these applications are limited to one kind of species and lack parallel detection capability.

The sensor array platform is highly innovative and versatile and has inspired by the novel uses. For example, for the point-of-care diagnostics applications it is envisioned that a microsystem-based sensors or parallel sensor array (2 to 64 channels and more); can be used for various species for shifts in resonance frequency of an array of cantilevers will be monitored as an indication of mass accumulation. In this example, detection of frequency shifts will be carried out through a novel integrated optoelectronic chip. Sensitivity in the range of 0.1 to 1000 ng/ml with better than 25% reproducibility is aimed. In addition to resonance frequency, one can measure the phase difference between the drive signal and the micro-cantilever motion. Cantilevers can be functionalized with various chemicals and can be placed in different channels. The same fluid can be applied to the channels where the effect of the chemicals is measured on fluid viscosity by monitoring the phase difference between the excitation signal and mechanical vibration waveform of the cantilevers in the array. Typical sensitivity of 0.001 cps is possible to achieve using cantilevers.

Additionally, possible use of this invention include liquid phase detection of disease from body fluids (e.g., blood, serum, urine, or saliva), and a detector to detect pathogens that may exists in environmental water supplies. Additionally, it is believed that in an aqueous medium, the invention will allow parallel, fast, real-time monitoring of a large number of analytes (e.g., proteins, pathogens, and DNA strands) without any need for labeling, and, therefore, be ideal for the targets screening in drug discovery process, or as a promising alternative to current DNA and protein micro array chips. Using such a label-free device may decrease the number of preparation stages and shorten diagnosis time. It is proposed that one can investigate DNA sequences, successful results will be the positive detection of various mutations in human DNA (e.g., sickle cell anemia, -thallesemia) in parallel.

This invention demonstrates a highly parallel detection of changes in the dynamics of a cantilever array. The proposed sensor can be used for label-free detection of (bio/chem) agents as well as liquid viscosity measurement in a robust, miniaturized package using multiple disciplines including integrated photonics, VLSI, and Micro/Nano system technologies to develop a versatile sensor array with breakthrough performance.

Each sensor is typically located on a MEMS sensor array operates by monitoring the resonant frequency, amplitude and/or phase of the vibrating mechanical structures (also called cantilevers or microcantilevers). Output of a sensor is the change in resonant frequency, amplitude and/or phase in response to accumulated mass on the cantilever due to a specific binding event or changes in the viscosity of the liquid. The array of cantilevers may be actuated by an actuating means, for example, electromagnetic force means; piezoelectric force; electric force; electrostatic force means and combinations thereof. The most preferred actuating means is a single electro-coil that carries a superposed drive current waveform. Preferably optical feedback from a mechanism to sense light coupled with each sensor is used for detection of specific binding events and also for closed-loop control of the cantilevers at resonance. More preferably, damping can be tuned by closed-loop control electronics allowing sharp resonance peaks (high-Q) even in liquid media. In a preferred embodiment, frequency resolution is inherently higher compared to other read-out techniques such as the piezoresistive or capacitive methods.

Preferably, the MEMS chip contains the functionalization layer on magnetic structural layer (for example, Nickel). More preferably, the location on the cantilever of the functionalized layer can be chosen to maximize the resonant frequency shift per added unit mass or the phase shift. In a preferred embodiment, the novel structure of the cantilevers includes a diffraction grating in the form of simple slits and/or heating elements. The light reflected from the diffraction grating can be collected by optical fibers. In another arrangement, diffraction gratings can be omitted and flat surface of the cantilevers can be used to reflect the light. In this case, light can be still collected using optical fibers where the cantilever vibration determines the amount of light coupling to the optical fibers and hence, the photodetector output that the fibers are coupled represents the cantilever vibration amplitude and phase. The MEMS sensor array (also called a MEMS chip) is preferably envisioned to be disposable and replaceable in future products; for example, as a disposable cartridge containing a MEMS sensor array to be coupled with a detector apparatus containing an actuating means (also sometimes called an actuator). This preferred embodiment would leave the actuator and electronics layers intact for reuse. Preferably, the MEMS chip is a passive component with no electronic link (also called an electrical conductor) to the detector apparatus. In this preferred embodiment this will facilitate work in fluidic environments, since less isolation, coupling, and stiction issues need to be considered. Furthermore, the preferred embodiment includes the integration of electronics and optics coupled with a passive component to provide ease and flexibility of use compared to a direct integration of the MEMS layer with IC detection apparatus. Finally in a preferred embodiment, magnetic actuation can be carried out remotely through an external electromagnetic coil on the MEMS chip. It is believed that sensitivity levels achieved in mass measurements will directly be reflected by detection sensitivity of the analytes of interest. Additionally, the type of surface functionalization utilized on the cantilever surfaces will determine the field of application, e.g., Human Kappa Opioid receptor (HKOR) is utilized for the detection of narcotics. In a preferred embodiment it is believed that a minimum mass detection limit of 500 femtograms or less may be achieved through discrete optics, electronics, and an electromagnet. Also the same system can achieve a low as 0.001 cps viscosity measurement sensitivity. Preferably, integration of discrete components and further miniaturization will substantially improve the minimum detection limit, sensitivity, parallelism, and robustness of the device and will meet the challenges of label-free and parallel detection in a portable device.

SUMMARY

It is an object of the present invention to provide a sensor that will work in disposable cartridges with remote sensing that can measure dynamic changes of the functionalized cantilevers in liquid and gas environment.

DESCRIPTION OF PREFERRED EMBODIMENTS

In a preferred embodiment the key areas of the system can be listed as follows: (1) A detector chip preferably including a silicon based novel integrated optoelectronic chip utilizing die-bonded laser diode array (1D VCSEL array), photodetectors 13, and CMOS readout electronics with wafer thinning and Si via technology; (2) A MEMS chip 1 (also called a MEMS sensor array) with micro/nano resonant cantilevers 10 with integrated grating 24 structures, heating elements 47 and, remote electromagnetic actuator for a disposable chip; (3) 3D integration of integrated optoelectronics chip and MEMS chip with hybrid-stacking, (4) Functionalization of MEMS cantilevers 10 with different specific recognition molecules (proteins, oligonucleotides, chemical assemblies) with focused immobilization methods addressing only one individual cantilever 10 from the array; (5) Demonstration of parallel sensor array operation (from 2 up to 64 parallel channels 16) for highly selective and accurate recognition of chemical and biological agents.

In a preferred embodiment involves the design and fabrication of the MEMS chip on SOI wafer with nickel cantilevers 10. The idea of an integrated diffraction grating 39 has already been demonstrated to provide extremely high-resolution displacement detection (with demonstrated sub-angstrom average detection limit) for Atomic Force Microscope (AFM) and other applications with simple fabrication and good immunity to environmental noise. In the preferred embodiment microcantilevers 38 can be replaced by membrane devices and in a preferred operation mode, cantilevers 10 or membranes can be coupled with an actuator to adjust the gap 26 to selectively tune the responsivity.

A preferred embodiment also involves optical fibers 32 to collect light. If the cantilevers 10 have gratings 24 than fibers 32 will collect light from the diffracted orders and couple it to photodectectors. For flat cantilevers 10, fibers 32 are also part of the detection mechanism. In this case, cantilever 10 vibration changes the direction of the light and hence affects the light coupled to the optical fiber 32.

A preferred embodiment also involves the design and fabrication of a detection apparatus comprising a detection chip and a control electronics 14 that functions independently of the MEMS layer. Preferably the detection apparatus is a universal read-out with no physical connection or electrical conductors to MEMS chip such that there is no electrical connection for electrons to flow from the detector chip or detector apparatus to the MEMS chip 1 and vice-versa. While VCSEL array technology is commercially available, it cannot be placed on the same side with the photodetectors 13 due to high packing density in the parallel sensor array and can be vertically integrated with flipchip bonding. Silicon via technology developed for 3D hybrid chip stacking will be utilized to channel 16 the VCSEL or other laser 27 onto MEMS chip. The preferably envisioned platform is versatile and can be utilized for optical interconnects and other photonics applications.

Preferably the detection apparatus includes a control electronics 14 involving closed loop control of MEMS cantilevers 10 using the detector chip with optical feedback at resonance, noise cancellation, and precise frequency measurement to detect dynamic changes. The detecting apparatus is preferably designed to be able to handle vapour phase and aqueous phase samples. The detector chip, preferably an optoelectronic chip, and the disposable MEMS layer are preferably aligned with good precision. Preferably this can be realized through mechanical guides machined in the package 2, and more preferably active alignment can be used to achieve few microns precision.

Preferably, control electronics 14 will drive the actuation means at a single frequency and the phase difference between the drive signal and the photodetector 13 signal will be measured.

Preferably, the individual components of the sensor array can each be optimally designed and manufactured and various noise reduction techniques can be implemented to achieve sensitivities approaching the fundamental limits. Developing compact, highly functional, portable and disposable sensors for bio-sensing, gas sensing, thermal sensing using an absorption area and thermal isolation legs, and spectroscopic devices using grating and selective absorbing materials with this sensor array technology. Hence, realization of the proposed ideas will contribute to a personal health system through multi-analyte diagnostics capability, increased effectiveness in doctor-patient interaction, early detection of diseases and their recurrence including cancer, and detection of hazardous substances for security.

Further exemplary embodiments are described below.

Figure 1:
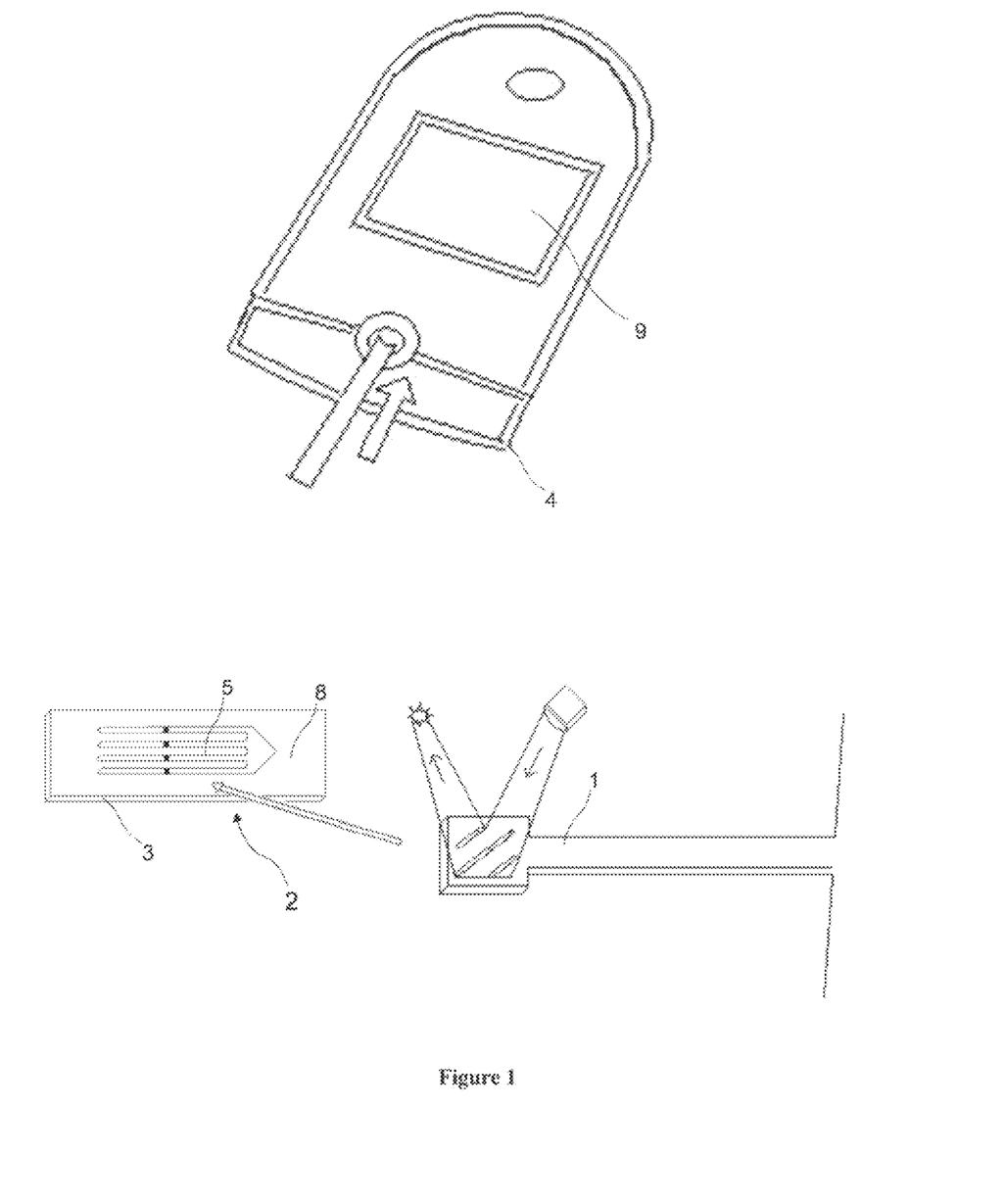
FIG. 1 is a diagrammatic view of a preferred embodiment of a system concept for the reader, cartridge and sensor with optical readout illustrating operation for liquid-phase sensing.

FIG. 1 shows a preferable disposable package 2 concepts and illustrates that there may be no electrical conductors (also called electrical connections) to the disposable cartridge 100. Likewise, microfluidics handling can be integrated (e.g., simple filtration can be used) with the disposable package 2 to separate serum from a drop of blood and then drive the serum onto the cantilevers 10 for measurement. The preferable reader 4 shown in FIG. 1 includes a detector apparatus and an actuating means 15 preferably an electromagnet 46 used for AC (alternating current) actuation and, preferably, a permanent magnet for magnetic field enhancement. The disposable package 2 shown in FIG. 1 also preferably includes a disposable cartridge 100 including a MEMS chip 1 coupled to a fluid contacting system preferably comprising a fluid chamber 5 (also sometimes called "a reaction chamber"), a fluid inlet coupled to the fluid chamber 5 and a fluid outlet also coupled to the fluid chamber 5. In some instance the fluid inlet and the fluid outlet may occur through the same space designated as a fluid inlet/outlet 8. The preferable reusable reader 4 also includes a mechanism to sense light which preferably is optoelectronic readout to measure the MEMS chip 1. The reader 4 also includes a pump that couples to fluid ports 8. The reader 4 also includes a temperature controller system to keep the cartridge at a desired temperature during testing. Further, the preferable reader 4 in FIG. 1 also preferably includes control electronics 14 and a user interface 9.

Figure 2:
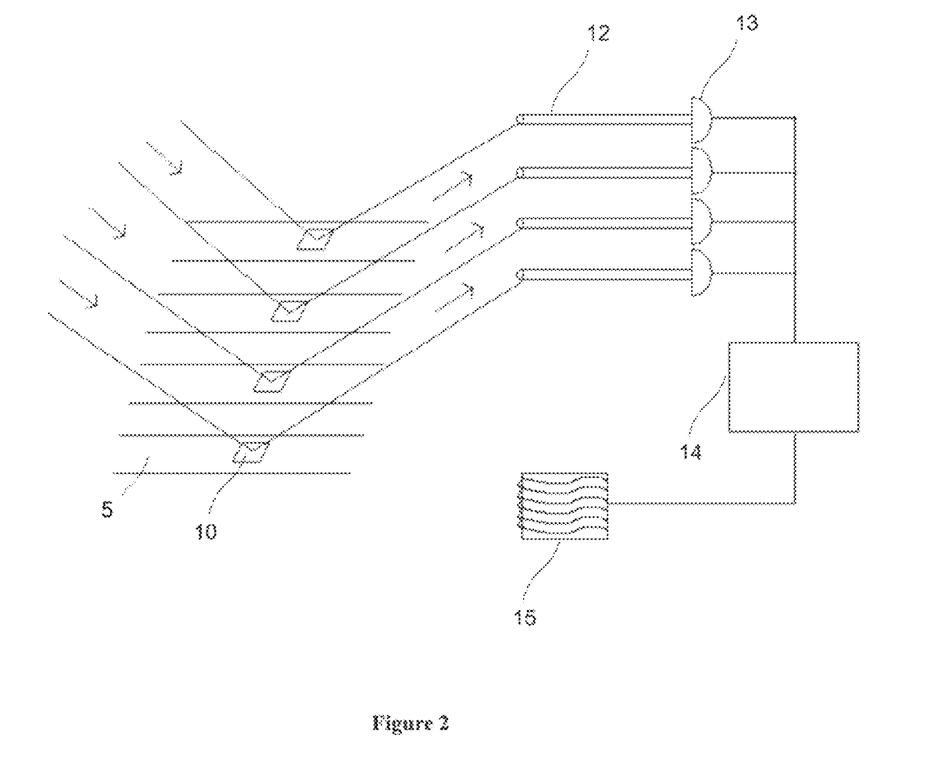
FIG. 2 is a diagram of one preferred embodiment of microcantilever array placed in a system of microfluidic channels including optical light collectors, actuation means and control electronics.

FIG. 2 shows details of a preferred embodiment of an optical readout and actuation means dramatically includes a disposable cartridge having cantilever 10 and fluid chambers 5, light collector 12, photodetector 13 and control electronics 14. An actuating means 15, preferably an electromagnet 46 and most preferably an electro-coil as shown, is placed below the cartridge that holds the microfluidic channels 22. The actuator may cause the cantilevers 10 to vibrate at certain frequencies. Also shown is a preferable laser 27 which couples to the cantilevers 10 and reflects from the cantilever 10 surface. The reflected light can be coupled to light collectors 12 which are coupled to photodetectors 13 for the detection of the reflected light. The signal output from the photodiode 33 is modulated by the cantilever 10 vibration. The cantilever 10 surface may have a grating 24. In this case the fibers 32 will collect the diffracted light from the gratings 24.

Figure 3:
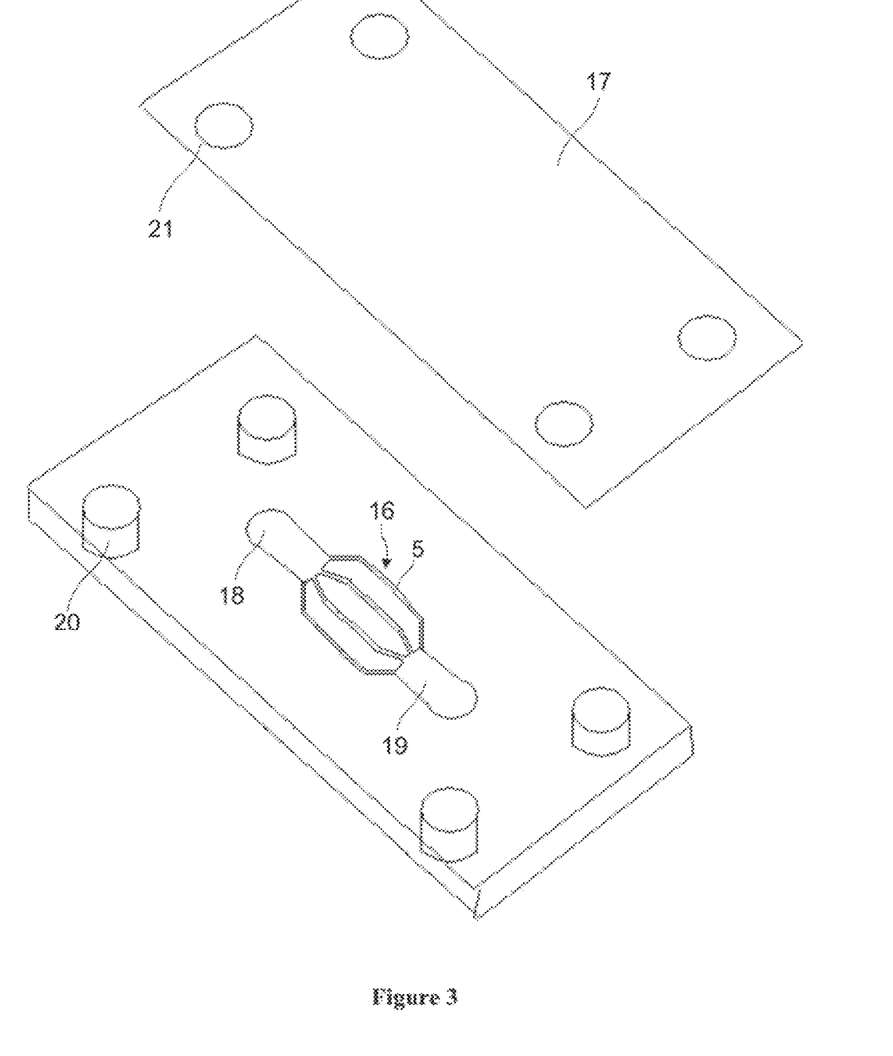
FIG. 3 is a diagrammatic view of one preferred embodiment of the invention including disposable cartridge.

FIG. 3 shows a disposable cartridge. The cartridge may have one of more channels 16 as shown in the figure. The channels 16 may have a fluidic chamber 5 where the width and/or height of the channel 16 are different from the rest of the channel 16. The cantilever 10 sensor can be placed in this portion of the channel 16. The cartridge material could be preferably plastic, epoxy glass, Plexiglas or acrylic. The channels 16 can be made by machining the disposable cartridge by mechanically, chemically or by molding techniques. A closed channel 16 can be obtained by gluing a cover plate 17 on the substrate 25 that holds the channels 16. The cartridge may have an inlet 18 and an outlet 19 coupled to the channels 16. The fluid can be applied through these openings as well as fluid motion can be achieved by coupling a pump to the inlet 18 or outlet 19. Inlet 18 and outlet 19 can be also placed on the cover. The cartridge may have alignment or guide cutouts 20 for easy placement of the cartridge into the reader 4. The cover may have the corresponding cutouts 21.

Figure 4:
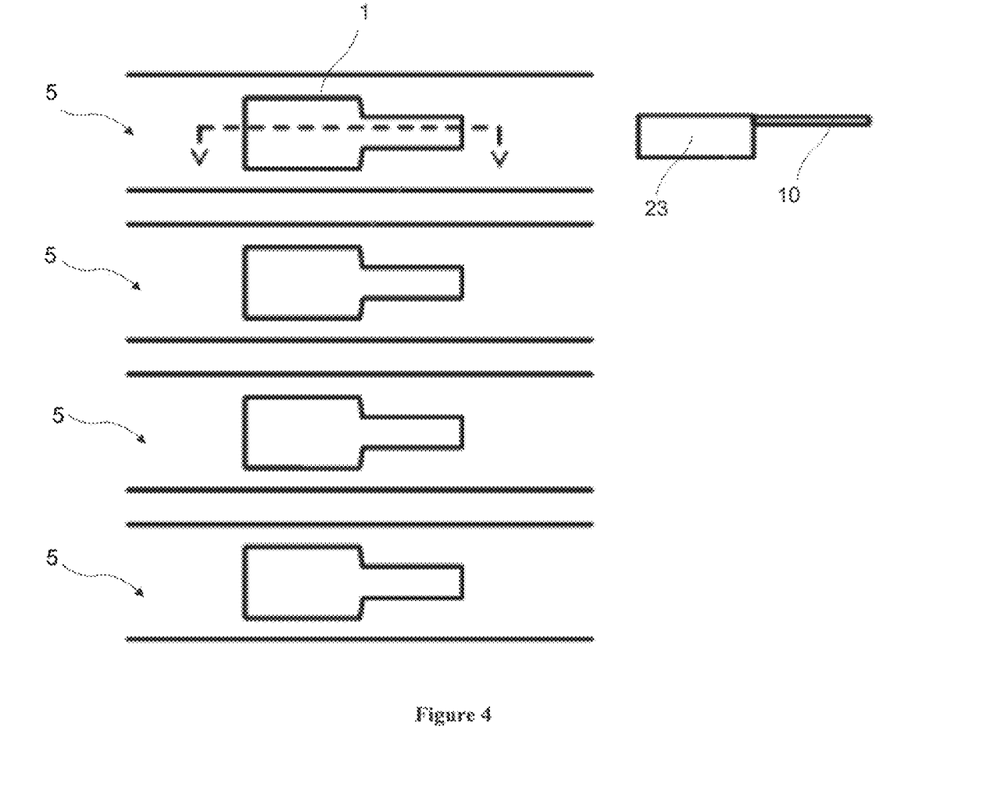
FIG. 4 is a diagrammatic top view of one preferred embodiment of the invention including MEMS sensors placed in microfluidic channels.

FIG. 4 shows top view of fluid channels 5 with MEMS chips 1. In a preferred embodiment, at least one MEMS chip can be placed in each fluid chamber 5. The MEMS chip is composed of the base 23, preferably silicon, and the cantilever 10, preferable a magnetic material.

Figure 5:
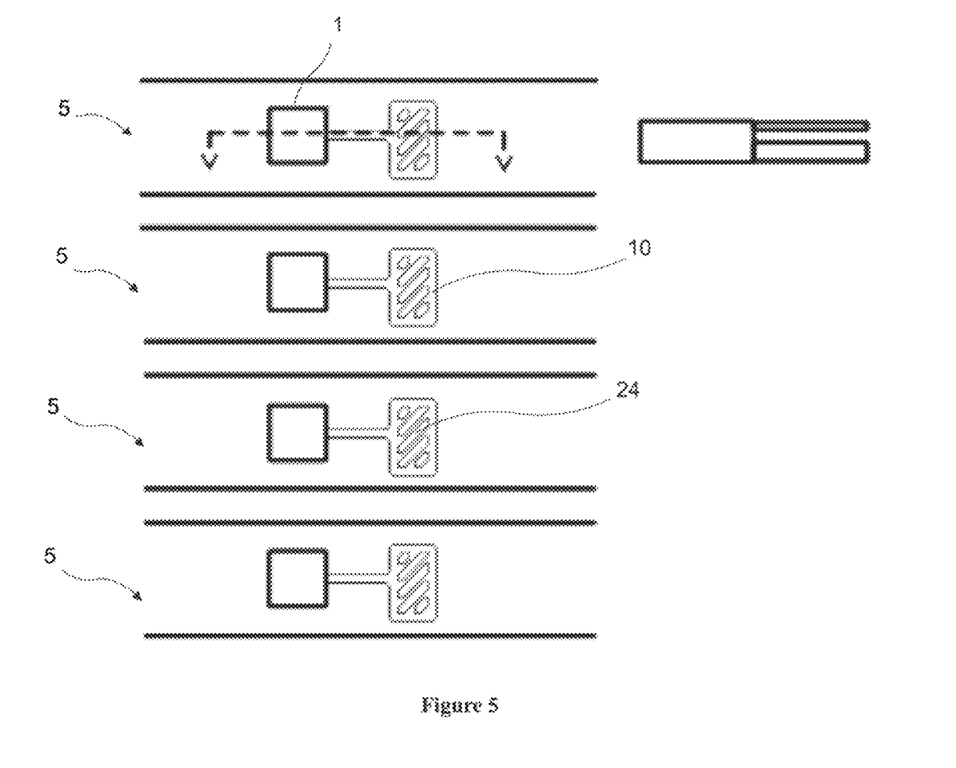
FIG. 5 is a diagrammatic to view of one preferred embodiment of the invention where MEMS microcantilevers have diffraction gratings at one end of the microcantilevers that are placed in microfluidic channels.

FIG. 5 shows the top view of MEMS chip 1 with gratings 24 at the end of the cantilevers 10. The cross section image shows the substrate 25 under the cantilever 10. This part is used for interference.

Figure 6:
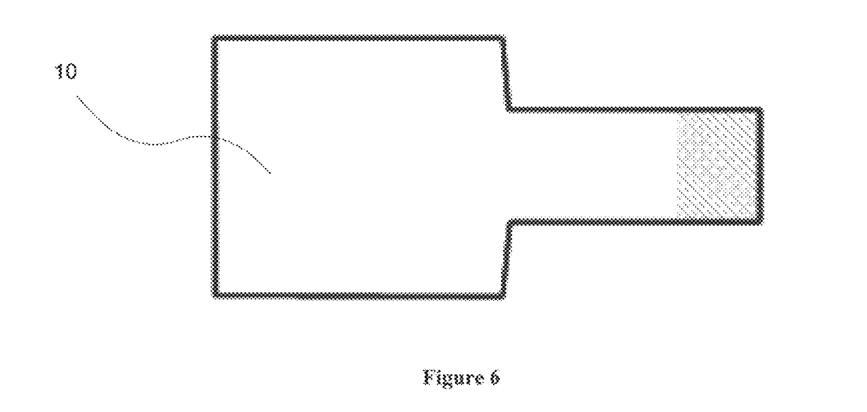
FIG. 6 is a diagrammatic view of one preferred embodiment of the cantilever where the tip of the cantilever is selectively functionalized with chemicals.

FIG. 6 shows a functionalized cantilever 10. The sensing surface of individual cantilevers 10 can be appropriately activated (self-assembled monolayer, hydrophilic polymer coating) for covalent immobilization of recognition molecules. In one embodiment, precise addressing of reagent solutions can be achieved using ink-jet deposition system, dip coating, microspotting, or using microfluidic channels 16 for each analyte; alternatively, photoactivation-based chemical reactions will be employed providing reactive groups only in the light-activated surface zones. It is envisioned that model (bio)ligands for covalent immobilization can include antibodies (immunosensing), oligonucleotide probes (hybridization assays) and chemical assemblies (nanotubes, nanoparticles, supermolecular complexes, lipid bilayers). It is believed that surface density of binding sites will be determined using enzyme labeling, fluorescent microscopic imaging and/or atomic force microscopy)

Figure 7:
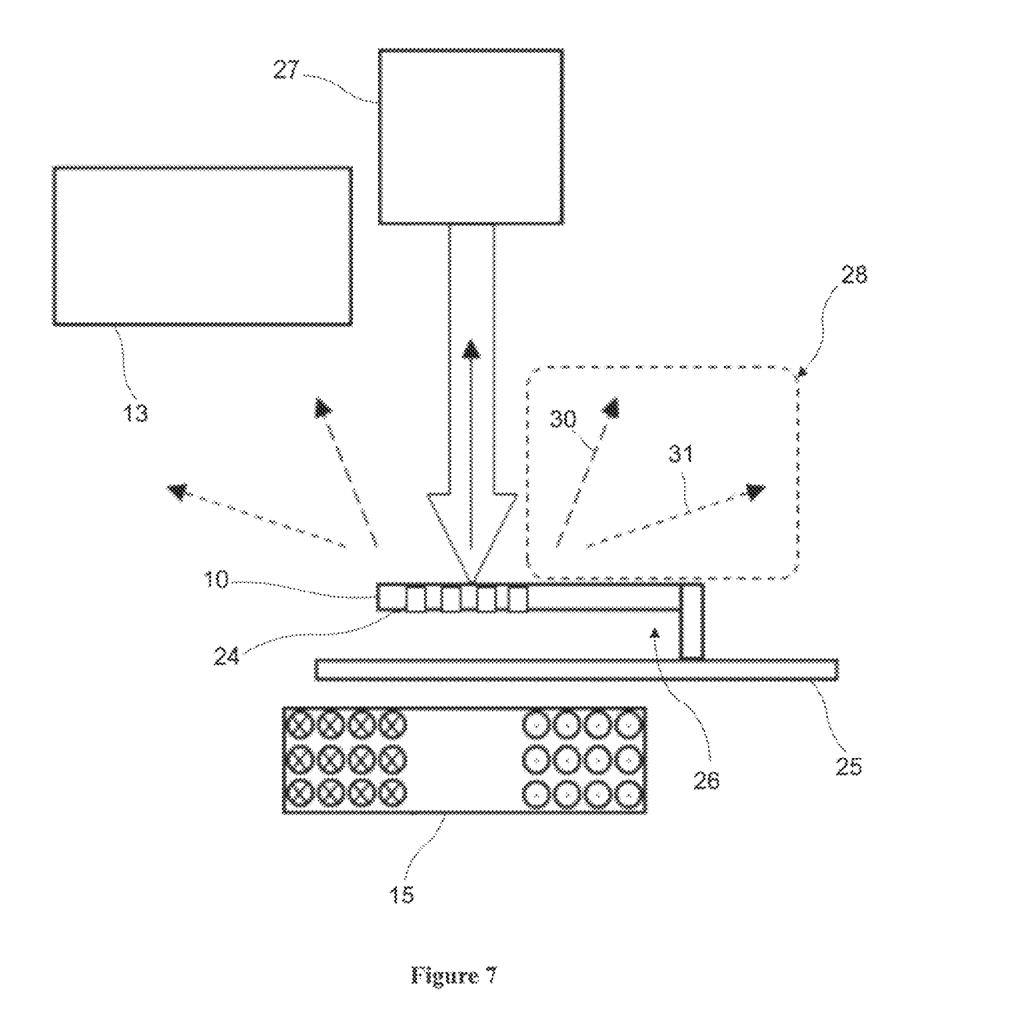
FIG. 7 is a diagrammatic view of a preferred embodiment of a system concept for an optical readout diagrammatically includes a cantilever having gratings.

FIG. 7 shows details of a preferred embodiment of an optical readout diagrammatically includes a cantilever 10 having grating 24 coupled to a substrate 25 to form a gap 26. An actuating means 15, preferably an electromagnet 46 and most preferably an electro-coil as shown, is placed below the substrate 25 which may cause the cantilever 10 to vibrate at certain frequencies. Also shown is a preferable laser 27 which couples to the grating 24 and forms refracted orders 28: $0^{th}$ order refraction, $1^{st}$ order retraction 30 and $3^{rd}$ order refraction 31 as preferably shown. The refracted orders 28 are collected by a combination of fiber optic cables 32 and photodetectors 13. The signal output from the photodiode 33 is represented by diffracted order intensities for the $0^{th}$ order refraction and the $1^{st}$ order refraction.

Figure 8:
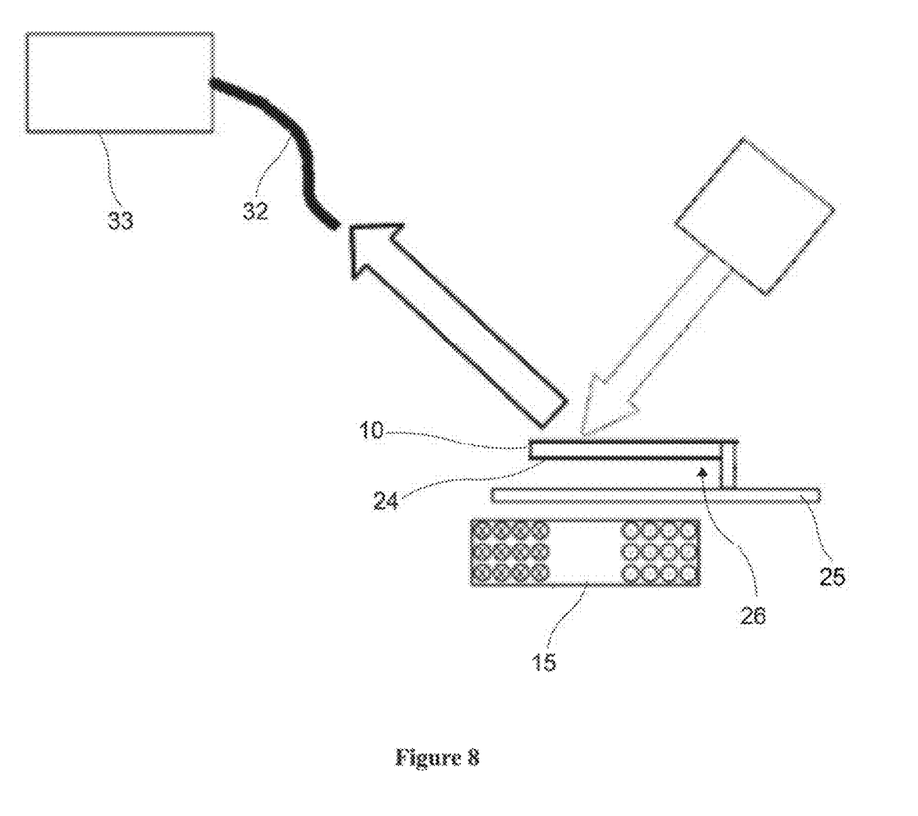
FIG. 8 is a diagrammatic view of a preferred embodiment of a concept using optical lever method to detect cantilever deflection where reflected light is collected by an optical fiber.

FIG. 8 shows details of a preferred embodiment of optical lever readout diagrammatically includes a cantilever 10 with a flat surface. An actuating means 15, preferably an electromagnet 46 and most preferably an electro-coil as shown, is placed below the disposable cartridge which may cause the cantilever 10 to vibrate at certain frequencies. Also shown is a preferable laser 27 which reflects back from the cantilever's 10 flat surface. The reflected beam is collected by an optical fiber 32. The vibration of the cantilever 10 changes the direction of the reflected light and hence changes the amount of light that couples to the fiber optic cable 32. The fiber optic cable 32 is coupled to photodiode 33 for detection. The signal output from the photodiode 33 is then modulated by the cantilever 10 vibration.

Figure 9:
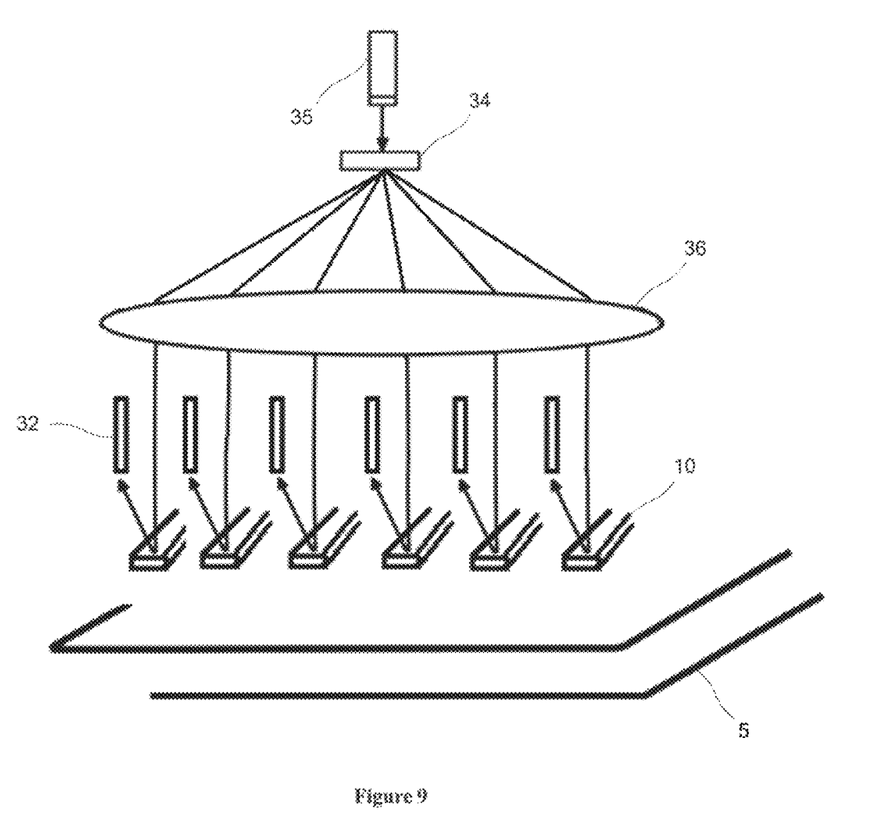
FIG. 9 is a diagrammatic view of a preferred embodiment of a concept illustrating optical illumination method where a fan-out diffraction grating is used to illuminate an array of microcantilevers.

FIG. 9 shows details of a preferred embodiment of an optical lever readout implemented for detecting vibration of an array of cantilevers 10 where cantilevers 10 are placed in a system of fluid chambers 5. A fan-out diffraction grating 34 can be used to generate multiple beams from a single light source 35, preferably a laser 27. A focusing optics 36 directs the generated beams onto cantilevers 10. The reflected light is collected byoptical fibers 32 which are couple to an array of photodiodes 33.

Figure 10:
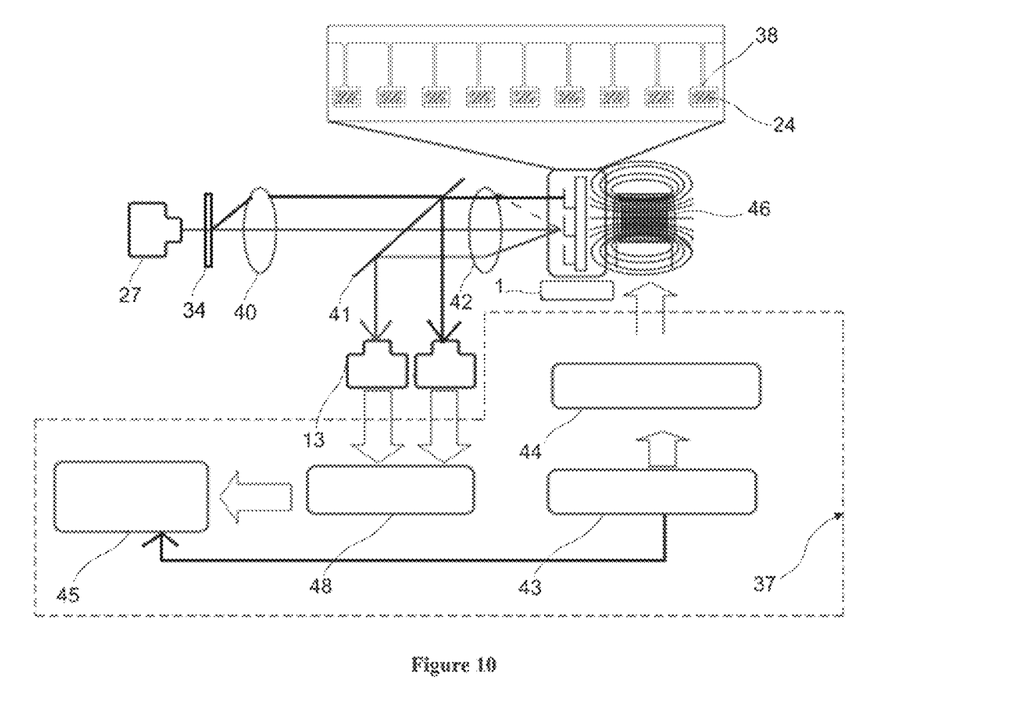
FIG. 10 is a diagrammatic view of a preferred embodiment showing the details of the parallel optical readout for cantilevers with diffraction gratings.

FIG. 10 illustrates the details of another preferred embodiment of electronics system 37 (may be part of the control electronics 14 and user interface 9 shown in FIG. 1) and the optical readout system (may also be known as the optoelectronic readout; for example as in FIG. 1), where the amplitude or the phase of the microcantilever 38 vibration of the microcantilever 38 is the desired sensor output. In this preferred embodiment, the optical readout system includes a laser 27, preferably a red laser diode, a diffraction grating 39, a first lens 40, a beam splitter 41 a second lens 42 and a photodetector 13, which can be coupled to a fiber 32, wherein the beam splitter 41 can interact with an individual grating 24 or the flat surface of the cantilever 10. In this preferred embodiment the microcantilevers 38 can be vibrated at a specific frequency at the vicinity of their resonances. The electronics system 37 includes a preamplifier 48 coupled to the photodetector 13 output, a signal generator 43 coupled to drive amplifier 44 and also coupled to phase and amplitude detection electronics 45, an electromagnet 46 that couples to the MEMS chip 1. In a preferred embodiment MEMS cantilevers 10 can be illuminated with a laser beam that is generated from a laser 27 using a fan-out diffraction grating 34. In the case of cantilevers 10 with gratings 24, reflected light from the substrate 25 and the sensor surface interfere and create diffraction orders. 1st diffraction order is monitored to avoid large bias in the 0th order direct reflection beam. The $1^{st}$ diffracted order is collected by a system of fiber cable 32 and photodiode 33. The photo diode signal is fed into a detection circuitry along with the reference drive output of the signal generator 43. The phase and amplitude detection electronics 45 then outputs the phase difference between the drive signal and the photodetector 13 output as well as the amplitude of the photodetector 13 signal. In the case of flat cantilevers 10, the optics is aligned such that the fibers 32 collect the reflected light from the cantilever 10 surface. The direction of the reflected light is determined by the cantilever 10 vibration therefore amount of coupled to the fiber 32.

Figure 11:
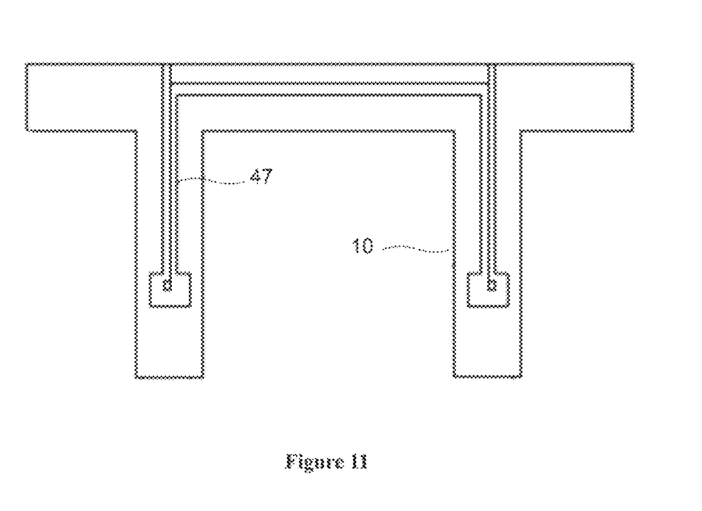
FIG. 11 is a diagrammatic view of a preferred embodiment of process layers for cantilever array, sensing layer, and local microheaters for the invention.

The preferred embodiment shown in FIG. 11 includes embedding heating element 47 in the cantilever 10 structure allows for local-heating on the cantilevers 10. This can be especially important for analyzing chemicals and biological samples as each reagent can have different adsorption and desorption rates at different temperatures. This can be used to improve specificity for selectivity) of detection against different chemical and biological binding events. Localized heating can be to create temperature dependent spectra, DNA melting curves, and to increase specificity by introducing multi-modal detection capability.

The invention claimed is:

1. A device adapted to sense mass accretion and viscosity comprising:
    a disposable cartridge having a plurality of fluidic channels,
    at least one vibrating mechanical structure placed in at least one fluidic channel,
    at least one light source coupled to each of the at least one vibrating mechanical structure,
    at least one actuation device being excited by a drive signal at a single actuation frequency,
    a control electronics measuring a vibrational phase of the vibrating mechanical structures with respect to an excitation signal from the actuation device,
    at least one light collector coupled to the at least one vibrating mechanical structure and the at least one light source,
    the at least one light collector being coupled to at least one photodetector and the control electronics being coupled to the at least one actuation device,
    wherein the at least one light collector collects light from the vibrating mechanical structure and couples to the light to said at least one photodetector;
    wherein the photodetector produces a photodetector signal;
    wherein the control electronics includes
        a phase and amplitude detection electronics;
        a preamplifier coupled to an output of the photodetector;
        a drive amplifier; and
        a signal generator coupled to the drive amplifier and also coupled to the phase and amplitude detection electronics;
        wherein the light source is coupled to a fan-out diffraction grating and a focusing optics;
        wherein the drive amplifier drives the actuation device at a single frequency and the phase and amplitude detection electronics outputs a phase difference between the drive signal and the photodetector signal.

2. The device in claim 1 wherein the control electronics is removably coupled to the at least one photodetector.

3. The device in claim 1 wherein the at least one light source is a single light source selected from the group consisting of laser source; VCSEL; LED and combinations thereof.

4. The device in claim 1 wherein the vibrating mechanical structures are suspended cantilevers.

5. The device in claim 4 wherein an unattached end of the cantilever contains an integrated grating.

6. The device in claim 4 wherein the cantilever surface is selectively functionalized.

7. The device in claim 1 wherein the vibrating mechanical structures bend in response to the actuation device and change the angle of reflected light.

8. The device in claim 1 wherein the at least one actuation device is selected from the group consisting of electromagnetic force; piezoelectric force; thermal force; electrostatic force and combinations thereof.

9. The device in claim 1 wherein the at least one actuation device is a single coil that energizes the at least one vibrating mechanical structure.

10. The device in claim 1 further comprising at least one heating element coupled with each vibrating mechanical structure.

11. The device in claim 1 wherein the disposable cartridge is temperature stabilized using a removably coupled temperature controller.

12. The device in claim 1 wherein the channels are selectively coated with different chemicals.

13. The device in claim 1 wherein the channels are connected to fluidic ports on the cartridge.

14. The device in claim 13 wherein a fluid in the channels is actuated by a pump removably coupled to the cartridge.

15. The device in claim 1 wherein the at least one actuation device is removably coupled to the at least one vibrating mechanical structure.

16. The device in claim 1 wherein the light collector is selected from waveguides, light guides, optical fibers and combinations thereof.

17. The device in claim 1 wherein the phase and amplitude detection electronics further outputs the amplitude of the photodetector output signal.

* * * * *